United States Patent
Ohashi et al.

(10) Patent No.: US 8,372,904 B2
(45) Date of Patent: Feb. 12, 2013

(54) ADSORPTIVE ULTRA-FINE METAL PARTICLES

(75) Inventors: Kazuaki Ohashi, Yokohama (JP); Kazuhiro Sato, Yokohama (JP); Munenori Ryo, Osaka (JP); Shigeru Suzuki, Osaka (JP)

(73) Assignee: Toyo Seikan Kaisha, Ltd., Tokyo (JP)

( * ) Notice: Subject to any disclaimer, the term of this patent is extended or adjusted under 35 U.S.C. 154(b) by 268 days.

(21) Appl. No.: 12/439,477

(22) PCT Filed: Sep. 3, 2007

(86) PCT No.: PCT/JP2007/067546
§ 371 (c)(1),
(2), (4) Date: Mar. 24, 2009

(87) PCT Pub. No.: WO2008/029932
PCT Pub. Date: Mar. 13, 2008

(65) Prior Publication Data
US 2010/0010130 A1    Jan. 14, 2010

(30) Foreign Application Priority Data
Sep. 1, 2006 (JP) .................... 2006-237898

(51) Int. Cl.
*C08K 5/00* (2006.01)
*C08F 299/00* (2006.01)
*B32B 15/00* (2006.01)
*B32B 15/01* (2006.01)
*B32B 15/08* (2006.01)

(52) U.S. Cl. .......... 524/176; 524/81; 524/322; 428/407; 556/114

(58) Field of Classification Search .................. 524/322, 524/176, 81; 428/407; 556/114
See application file for complete search history.

(56) References Cited

U.S. PATENT DOCUMENTS

| | | | |
|---|---|---|---|
| 4,186,244 A | 1/1980 | Deffeyes et al. | |
| 6,294,602 B1 * | 9/2001 | Shimo et al. | 524/394 |
| 6,358,611 B1 | 3/2002 | Nagasawa et al. | |
| 2002/0018896 A1 * | 2/2002 | Fukunaga et al. | 428/407 |
| 2004/0173666 A1 | 9/2004 | Fukunaga et al. | |
| 2004/0245648 A1 | 12/2004 | Nagasawa et al. | |
| 2005/0112155 A1 | 5/2005 | Giroud et al. | |
| 2007/0225409 A1 * | 9/2007 | Matsumoto | 524/81 |

FOREIGN PATENT DOCUMENTS

| | | |
|---|---|---|
| EP | 1452188 A1 | 9/2004 |
| EP | 1579935 A1 | 9/2005 |
| JP | 5-247258 A | 9/1993 |
| JP | 9-75434 A | 3/1997 |
| JP | 10-183207 A | 7/1998 |
| JP | 2000-327836 A | 11/2000 |
| JP | 2004-156020 A | 6/2004 |
| JP | 2006-021450 A | 1/2006 |
| JP | 2006-109902 A | 4/2006 |
| JP | 2006/080319 * | 8/2006 |
| JP | 2006-348213 A | 12/2006 |
| WO | 01/70435 A1 | 9/2001 |
| WO | WO2005/085358 * | 9/2005 |
| WO | 2006/080319 A1 | 8/2006 |

* cited by examiner

*Primary Examiner* — James J Seidleck
*Assistant Examiner* — Deve E Valdez
(74) *Attorney, Agent, or Firm* — Sughrue Mion, PLLC (57) ABSTRACT

Adsorptive ultra-fine metal particles having a bond between an organic acid component and a metal, and exhibiting an infrared absorption peak derived from the bond between the organic acid component and the metal near 1518 $cm^{-1}$. The adsorptive ultra-fine metal particles are capable of exhibiting excellent deodorizing property and VOC-adsorbing property without impairing properties and formability of the resin. The invention is further concerned to an adsorptive resin composition and an adsorptive coating material containing the adsorptive ultra-fine metal particles and are capable of forming shaped resin articles or coatings.

3 Claims, 4 Drawing Sheets

ADSORPTIVE ULTRA-FINE METAL PARTICLES

TECHNICAL FIELD

This invention relates to adsorptive ultra-fine metal particles and, more specifically, to adsorptive ultra-fine metal particles which, when blended in a resin, are capable of exhibiting excellent adsorbing property without impairing properties and formability of the resin.

BACKGROUND ART

A variety of deodorants or adsorbents have heretofore been proposed that are capable of adsorbing offensive odor components such as methyl mercaptan and the like, as well as volatile organic compounds (hereinafter referred to as "VOCs") such as formaldehyde and the like, the deodorants or the absorbents, usually, using a porous material such as active carbon, silica, zeolite or the like.

Various shaped articles have also been proposed blended with a thermoplastic resin to impart properties for adsorbing the above components.

For example, as disclosed in JP-A-9-75434, active carbon, inorganic filler such as porous zeolite or sepiolite, and titanium oxide utilizing a photocatalytic action, are capable of deodorizing a wide range of bad-smelling components and have heat resistance enabling themselves to be melted and kneaded with a thermoplastic resin.

Moreover, a deodorant using ultra-fine metal particles has been proposed. JP-A-2006-109902 proposes a deodorant using, as an effective component, a colloidal solution of ultra-fine metal particles obtained by reducing a solution containing metal ions.

DISCLOSURE OF THE INVENTION

However, the one that utilizes a porous material produces its adsorptive effect (deodorizing effect) upon adsorbing the bad-smelling components or VOCs and is, therefore, accompanied by a problem in that the effect extinguishes if the adsorptive sites are saturated. The inorganic filler must use a dispersant at the time when it is to be melted and kneaded with a thermoplastic resin in order to improve the dispersion property and is, therefore, accompanied by a problem in that the adsorptive effect greatly decreases as the adsorptive sites on the surface of the inorganic filler are covered with the resin or the dispersant.

The deodorant which utilizes the photocatalytic action has a problem in that the surface of the titanium oxide must have been irradiated with ultraviolet rays at all times for decomposing and deodorizing the bad-smelling components.

Further, when the deodorant that employs ultra-fine metal particles is used being blended in a resin, the resin is decomposed by ultra-fine metal particles having a high surface activity, the formability is greatly impaired and, besides, a dispersing solution is necessary from the standpoint of handling, which, therefore, is far from satisfactory for being blended in the resin.

It is, therefore, an object of the present invention to provide adsorptive ultra-fine metal particles capable of exhibiting excellent adsorptive effect (deodorizing effect) without impairing properties and formability of a resin.

Another object of the present invention is to provide an adsorptive resin composition and an adsorptive coating material containing the above adsorptive ultra-fine metal particles, and are capable of forming shaped resin articles or coatings.

A further object of the present invention is to provide adsorptive ultra-fine metal particles capable of effectively adsorbing bad-smelling components such as methyl mercaptan and the like, as well as VOCs.

According to the present invention, there are provided adsorptive ultra-fine metal particles having a bond between an organic acid component and a metal, and exhibiting an infrared absorption peak derived from the bond between the organic acid component and the metal near 1518 $cm^{-1}$.

According to the adsorptive ultra-fine metal particles of the present invention, it is desired that:

1. The organic acid component is a higher fatty acid; and
2. The metal is at least any one of gold, silver or copper.

According to the invention, further, there is provided an adsorptive resin composition that contains the above adsorptive ultra-fine metal particles. In the adsorptive resin composition, it is desired that the resin that contains the adsorptive ultra-fine metal particles has a coefficient of oxygen permeation of not smaller than $1.0 \times 10^{-4}$ cc·m/m²·day·atm.

According to the present invention, there is further provided an adsorptive coating material containing the above adsorptive ultra-fine metal particles.

An important feature resides in that the adsorptive ultra-fine metal particles of the invention are ultra-fine metal particles having a bond between an organic acid component and a metal, and exhibiting an infrared absorption peak derived from the bond between the organic acid component and the metal near 1518 $cm^{-1}$.

Ultra-fine metal particles of particle diameters of not larger than 1000 nm have properties that are greatly different from those of ordinary metal particles and, particularly, have high surface activities and large surface areas exhibiting, therefore, excellent reactivity with bad-smelling components or VOCs, rate of adsorption and amount of adsorption larger than those of ordinary particles, and offering excellent adsorptive effect. As described above, however, because of their very high surface activities, the ultra-fine metal particles promote the decomposition of a resin if they are blended in the resin to seriously impair the formability of the resin.

According to the present invention, however, an organic acid component is made present on the surfaces of the ultra-fine metal particles to decrease the direct contact between the metal surfaces and the resin, to effectively suppress the decomposition of the resin, to prevent a decrease in the molecular weight of the resin and, therefore, to prevent the formability from being impaired.

Further, the resin composition containing the adsorptive ultra-fine metal particles of the invention makes it possible to attain nano particles and nano dispersion directly in the resin without using a dispersing solution that is used for the conventional ultra-fine metal particles. That is, according to the present invention, it was discovered that an organic acid metal salt turns into ultra-fine metal particles through the self reduction or the pyrolysis in the step of heat-forming the resin or in the step of forming a coating, and that by blending the resin with the organic acid metal salt followed by kneading using an extruder or followed by baking the coating material, the organic acid metal salt turns into nano particles through the pyrolysis and is nano-dispersed without aggregating again, and nano particles and nano dispersion are efficiently realized in the resin simultaneously with the forming.

This is obvious from the results of Examples described later. For example, from FIGS. 3 and 4 which are transmission-type electron microphotographs of sectional surfaces of films obtained in Examples 2 and 4, it is obvious that ultra-fine metal particles (dark portions) (nano particles) have been formed in the films. From FIG. 5 which is a scanning-type electron microphotograph of a surface of a film obtained in Example 11, further, it is obvious that ultra-fine metal particles (white portions) are homogeneously and finely dispersed (nano dispersion).

Figure 1:
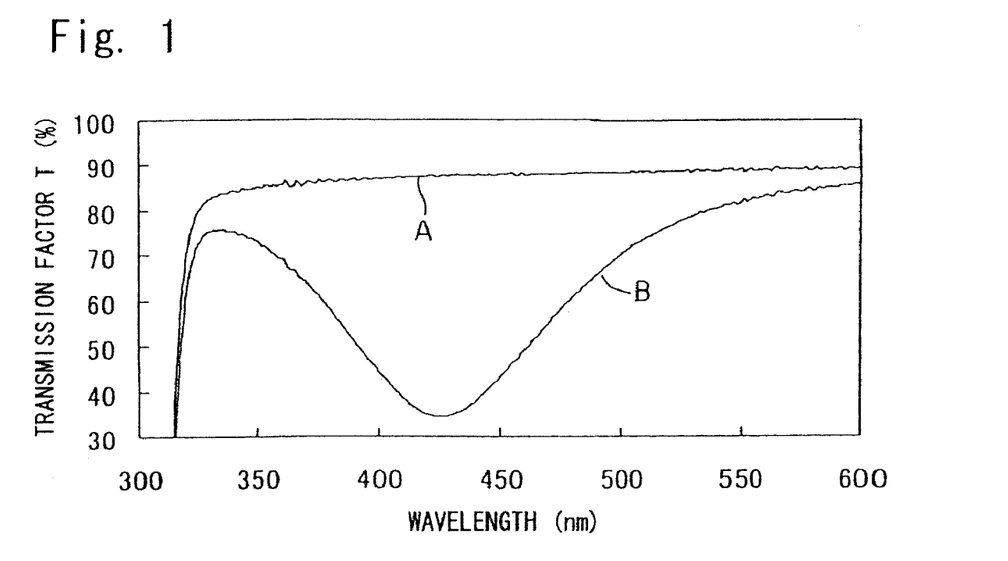
FIG. 1 is a diagram illustrating spectral transmission factor curves for confirming nano dispersion.

The fact that the ultra-fine metal particles have been nano-dispersed in the resin can be confirmed from the presence of plasmon absorption of nano particles. FIG. 1 shows spectral transmission factor curves of a film comprising a polyethylene terephthalate only, and a film obtained by adding 0.5% by weight of a silver myristate of an average particle diameter of 100 μm to the polyethylene terephthalate, and biaxially extruding the polyethylene terephthalate at 270° C. to disperse ultra-fine metal particles having an average particle diameter of 50 nm therein. It will be obvious from FIG. 1 that no peak is formed in the case of the simple polyethylene terephthalate A while a peak is obtained near 400 to 450 nm in the case of the polyethylene terephthalate B containing the silver myristate, from which it can be confirmed that the silver particles have been nano-dispersed in the polyethylene terephthalate.

The average particle diameter referred to in this specification is an average value of the particles that have no gap between a metal and a metal.

The adsorptive ultra-fine metal particles of the present invention are capable of exhibiting excellent adsorbing property (inclusive of deodorizing property, in this specification the concept of "adsorbing property" includes "deodorizing property") without impairing properties and formability of the resin. Besides, the adsorptive ultra-fine metal particles of the present invention are capable of attaining nano particles and nano dispersion upon the heating at the time of forming without requiring dispersing solution, and make it possible to strikingly improve the formability.

Further, the adsorptive resin composition and the adsorptive coating material containing the adsorptive ultra-fine metal particles are capable of forming shaped resin articles or coatings, and of attaining nano particles and nano dispersion simultaneously with the forming of shaped articles or the coatings, featuring excellent productivity, and enabling the obtained shaped articles or the coatings to exhibit excellent adsorptive property.

The adsorptive ultra-fine metal particles of the invention are capable of effectively adsorbing bad-smelling components and VOCs, and exhibit excellent deodorizing property or VOC-adsorbing property.

BEST MODE FOR CARRYING OUT THE INVENTION

Ultra-Fine Metal Particles

In the adsorptive ultra-fine metal particles of the present invention, there is no particular limitation on the metal components of ultra-fine metal particles, and there can be exemplified Cu, Ag, Au, In, Pd, Pt, Fe, Ni, Co. Nb, Ru, Rh and Sn. Among them, Au, Ag, Cu, Pt and Sn are preferred. These metal components may be simple substances, mixtures or alloys.

In the present invention, an important feature resides in that the metal has a bond with the organic acid. As the organic acid, there can be exemplified aliphatic carboxylic acids such as myristic acid, stearic acid, oleic acid, palmitic acid, n-decanoic acid, para-toluic acid, succinic acid, malonic acid, tartalic acid, malic acid, glutalic acid, adipic acid and acetic acid; aromatic carboxylic acids such as phthalic acid, maleic acid, isophthalic acid, terephthalic acid, benzoic acid and naphthenic acid; alicyclic carboxylic acids such as cyclohexanedicarboxylic acid and the like.

In the present invention, it is particularly desired that the organic acid that is used is a higher fatty acid such as myristic acid, stearic acid or palmitic acid. Upon having branches and many carbon atoms, the organic acid component itself adsorbs bad-smelling components and VOCs, and exhibits further improved adsorptive effect (deodorizing effect).

As the organic acid metal salt which is a preferred starting material of ultra-fine metal particles, there can be particularly exemplified a silver myristate or a silver stearate having an average particle diameter in a range of 1 to 500 μm and, particularly, 10 to 200 μm.

As for the ultra-fine metal particles of the invention, simple ultra-fine metal particles can be formed by heat-treating an organic acid metal salt which is a starting material of the ultra-fine metal particles in an inert gas atmosphere. Preferably, the organic acid metal salt is mixed with a thermoplastic resin and is heat-treated to form ultra-fine metal particles in the form of nano particles which are nano-dispersed in the resin.

The heating conditions necessary for obtaining the ultra-fine metal particles of the invention may vary depending upon the organic acid metal salt that is used and cannot be definitely defined but, generally, consist of heating at a temperature of 120 to 350° C. and, particularly, 170 to 300° C. for 1 to 1800 seconds and, particularly, 10 to 600 seconds.

It is desired that the ultra-fine metal particles of the invention have a maximum diameter of smaller than 1 μm and an average particle diameter in a range of, particularly, 1 to 100 nm.

(Adsorptive Resin Compositions)

The adsorptive resin composition of the present invention is an adsorptive resin composition capable of forming shaped resin articles containing the above-mentioned adsorptive ultra-fine metal particles of the invention, and may be the one obtained by blending a resin with the ultra-fine metal particles that are obtained by heat-treating the organic acid metal salt in an inert atmosphere but is, particularly desirably, a resin composition containing the organic acid metal salt which is the starting material of the above ultra-fine metal particles.

That is, as described above, the organic acid metal salt which is the starting material of the adsorptive ultra-fine metal particles of the invention turns into nano particles that are nano-dispersed in the formed resin article through the heat treatment at the time of forming the resin composition enabling the adsorptive ultra-fine metal particles of the invention to be present in the formed resin article.

As the resin that contains the adsorptive ultra-fine metal particles of the invention, there can be used any known thermoplastic resin that can be melted and formed, i.e., olefin resins such as low-, intermediate- and high-density polyethylenes, linear low-density polyethylene, linear ultra-low density polyethylene, isotactic polypropylene, syndiotactic polypropylene, propylene/ethylene copolymer, polybutene- 1, ethylene/butene-1 copolymer, propylene/butene-1 copolymer and ethylene/propylene/butene-1 copolymer; polyester resins such as polyethylene terephthalate, polybutylene terephthalate and polyethylene naphthate; polyamide resins such as nylon 6, nylon 6,6 and nylon 6,10; and polycarbonate resins.

In the adsorptive resin composition of the present invention, it is particularly desired that the resin has an oxygen permeation coefficient of not smaller than $1.0 \times 10^{-4}$ cc·m/m$^2$·day·atm. This enables the adsorptive ultra-fine metal particles to easily adsorb bad-smelling components or VOCs and to further improve adsorbing property.

It is particularly desired to use a polyethylene for the adsorptive resin composition of the present invention.

Depending upon the use, further, the adsorptive resin composition of the invention may be blended with known blending agents such as filler, plasticizer, leveling agent, viscosity-imparting agent, viscosity-reducing agent, stabilizer, antioxidant and ultraviolet-ray absorber according to known recipes.

It is desired that the adsorptive resin composition of the present invention is blended with the organic acid metal salt in an amount of 0.01 to 5 parts by weight per 100 parts by weight of the resin. If the amount thereof is smaller than the above range, the adsorptive effect is not obtained to a sufficient degree. If the amount thereof is larger than the above range, on the other hand, the metal particles coagulate and nano dispersion cannot be attained, which is not desirable.

The adsorptive resin composition of the present invention can be subjected to a known melt-forming, such as two-roll method, injection forming, extrusion forming or compression forming to obtain an adsorptive (deodorizing) shaped resin article in a form that meets the use of the final shaped article, such as granules, pellets, film, sheet, container, building material, wall paper, etc.

The temperature for forming the shaped resin article may vary depending upon the forming method and the kinds of resin and organic acid metal salt, and cannot be definitely specified, but must be such a temperature that does not thermally deteriorate the resin that is used, and must be in the above-mentioned temperature range in which the organic acid metal salt turns into nano particles so as to be nano-dispersed.

Further, the adsorptive resin composition of the invention by itself may constitute an adsorptive shaped resin article but can also be used in combination with other resins to realize a multi-layer structure.

The resin shaped articles formed by using the adsorptive resin composition of the invention have excellent deodorizing property and VOC-adsorbing property attaining nano particles and nano dispersion simultaneously with the forming, and can be excellently produced.

(Adsorptive Coating Materials)

The adsorptive coating material of the present invention is an adsorptive coating material capable of forming a coating containing the above-mentioned adsorptive ultra-fine metal particles of the invention, and may be the one obtained by blending the coating components with the ultra-fine metal particles that are obtained by heat-treating the organic acid metal salt in an inert atmosphere but is, particularly desirably, a coating material containing an organic acid metal salt which is the starting material of the above ultra-fine metal particles.

That is, as described above, the organic acid metal salt which is the starting material of the adsorptive ultra-fine metal particles of the invention turns into nano particles that are nano-dispersed in the coating components through the heat treatment at the time of baking the coating enabling the adsorptive ultra-fine metal particles of the invention to be present in the coating.

It is desired that the adsorptive coating material of the present invention is blended with an organometal compound such as organic acid metal salt in an amount of 0.01 to 5 parts by weight per 100 parts by weight of the coating components. If the amount thereof is smaller than the above range, the adsorptive effect is not obtained to a sufficient degree. If the amount thereof is larger than the above range, on the other hand, the ultra-fine metal particles coagulate, which is not desirable.

As the coating components to be blended with the organometal compound such as organic acid metal salt, any material can be used if it is capable of forming a coating upon heating. Though not limited thereto only, there can be used known coating compositions such as acrylic coating material, epoxy coating material, phenol coating material, urethane coating material, polyester coating material and alkyd resin coating material.

The conditions for heat-treating the coating material may vary depending upon the kinds of the coating components and the organic acid metal salt that are used and cannot be definitely defined but, generally, consist of heat-treating the coating material at a temperature in a range which does not cause thermal deterioration and in which the organic acid metal salt turns into nano particles which are nano-dispersed for 60 to 600 seconds.

The coating obtained from the adsorptive coating material of the invention has excellent deodorizing property and VOC-adsorbing property attaining nano particles and nano dispersion simultaneously with the forming of the coating, and can be excellently produced.

EXAMPLES

1. Conversion into the Amount of Methyl Mercaptan in a Purge-and-Trap Gas Chromatograph Mass Spectrometer (P&T-GCMS)

Figure 2:
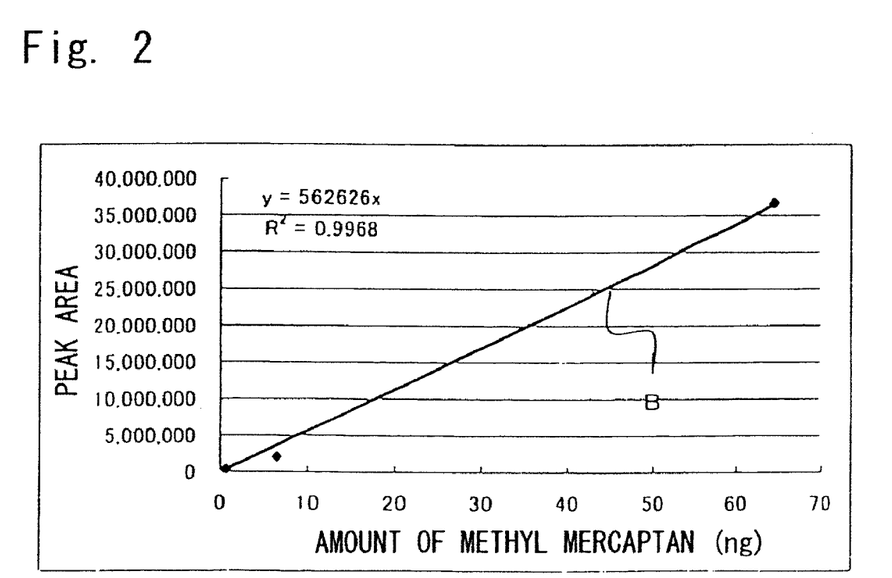
FIG. 2 is a diagram showing a calibration curve found from the methyl mercaptan concentrations and the peak areas.

Aqueous solutions of methyl mercaptan of concentrations of 65 ppm, 6.5 ppm and 0.65 ppm were picked up each in an amount of 1 μL, and were measured and confirmed for their peak areas derived from the methyl mercaptan by using a purge-and-trap gas chromatograph mass spectrometer (P&T-GCMS) to obtain the results as shown in Table 1. The unit ppm of concentrations of the aqueous solutions is ng/μL. A calibration curve was found from the concentrations (amounts) (x) of the methyl mercaptan and the peak areas (y).

$y = 562626x$
$R = 0.9968$

The calibration curve is shown in FIG. 2.

TABLE 1

| Injected amount | Concentration of methyl mercaptan aq. sol. (ppm) | Weight (ng) of methyl mercaptan in 1 μL | Peak area |
|---|---|---|---|
| 1 μL | 65 | 65 | 36,726,852 |
| 1 μL | 6.5 | 6.5 | 2,022,414 |
| 1 μL | 0.65 | 0.65 | 387,688 |

2. Measuring the Particle Diameters

Figure 3:
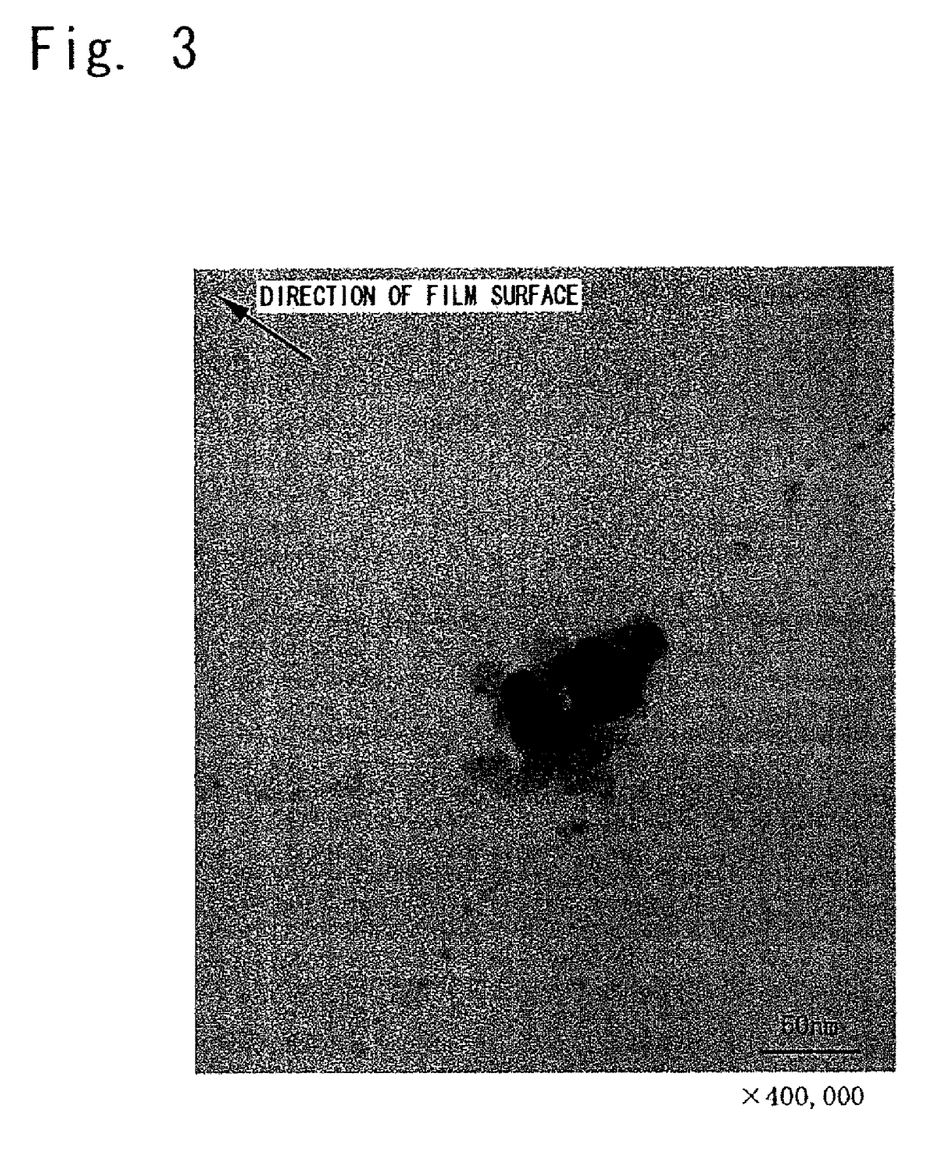
FIG. 3 is a transmission-type electron microphotograph of a cross section of a film obtained in Example 2.
Figure 4:
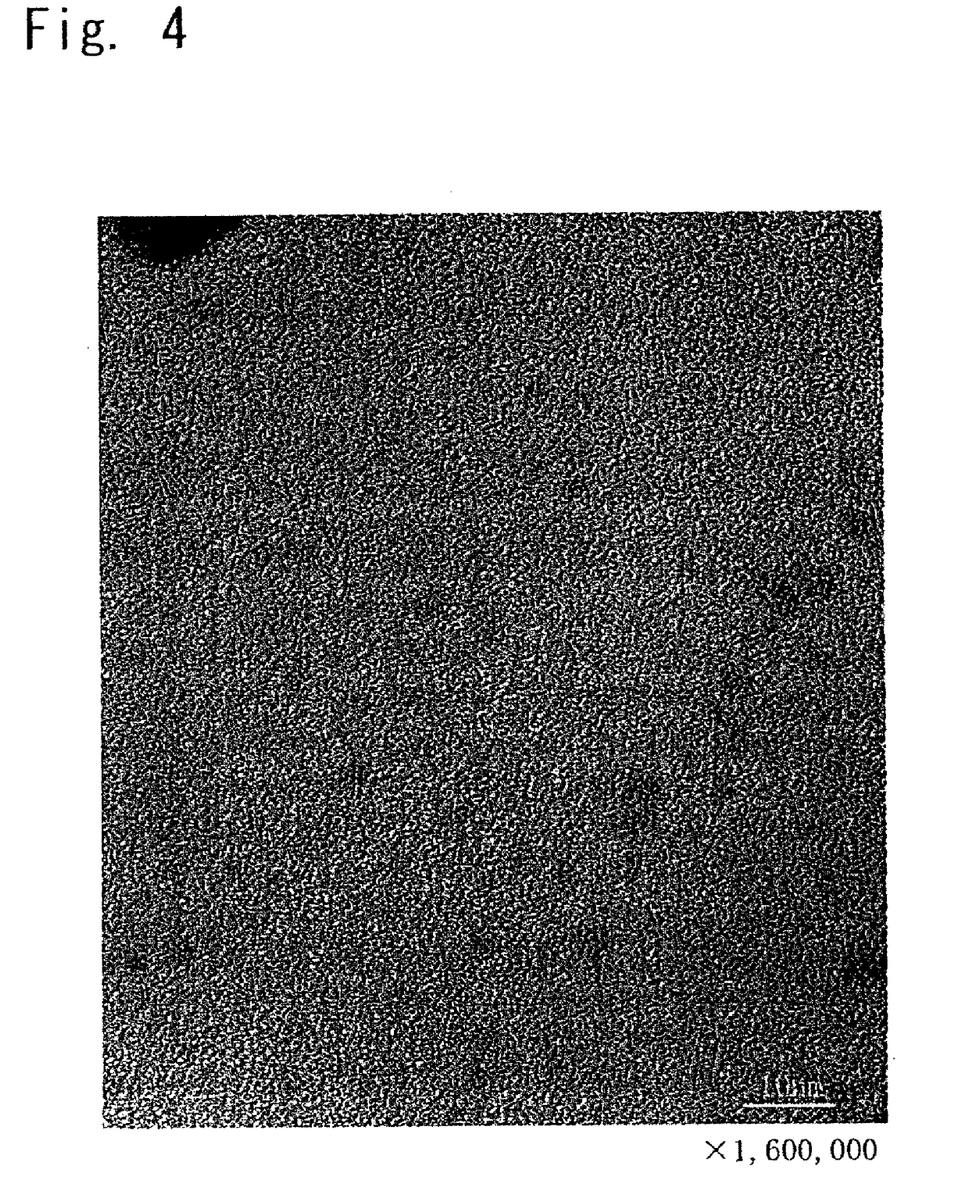
FIG. 4 is a transmission-type electron microphotograph of a cross section of a film obtained in Example 4.
Figure 5:
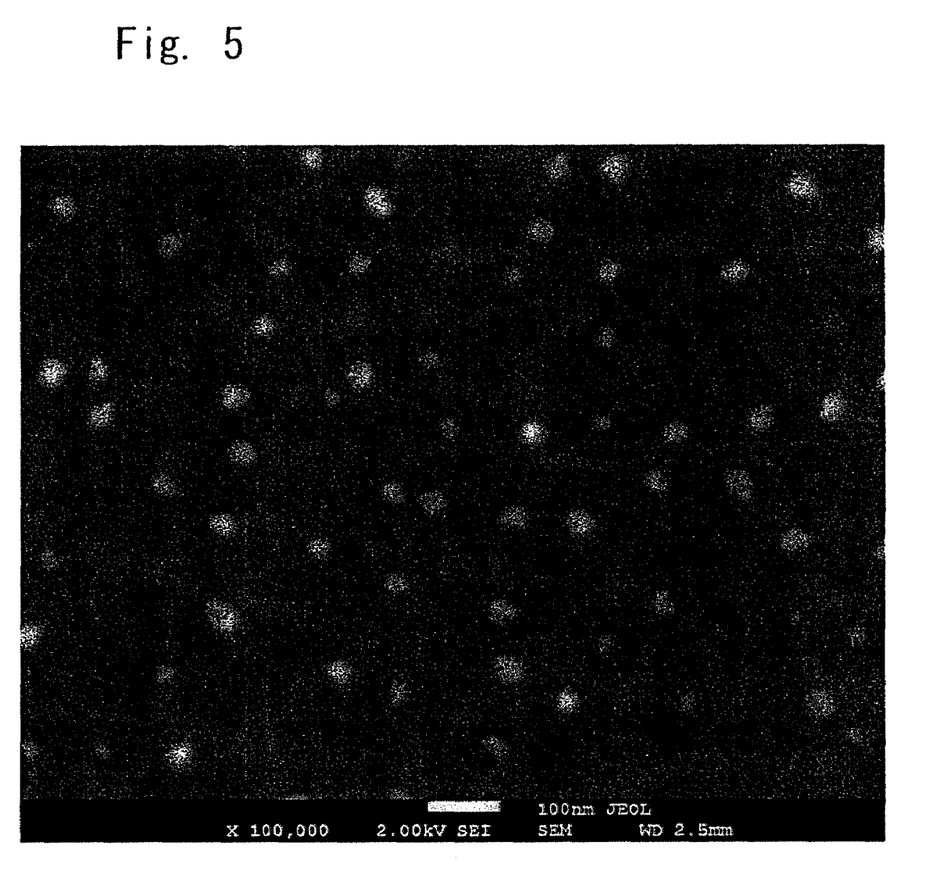
FIG. 5 is a scanning-type electron microphotograph of a surface of a film obtained in Example 11.

Films obtained in Examples 1 to 8, 10 to 15 and in Comparative Examples 1 to 12 and a primer coating of a primer-coated film obtained in Example 9 were sliced in a direction of cross section, and were observed by using a transmission-type electron microscope (TEM) to obtain TEM photographs of the observed ultra-fine metal particles (TEM photographs of Examples 2 and 4 are shown in FIGS. 3 and 4 as representative examples). Ultra-fine metal particles in the photographs were measured for their average particle diameters by using an image analytical software for measuring particle profile: mac-view.

3. Measuring the Amounts of Methyl Mercaptan

The films obtained in Examples 1 to 8, 10 to 15 and in Comparative Examples 1 to 12 and the primer-coated film obtained in Example 9 were introduced into a 500-mL glass bottle purged with a nitrogen gas, and were sealed with a rubber plug. Thereafter, 5 μL of a methyl mercaptan of a concentration of 650 ppm was injected as a bad-smelling substance into the bottle by using a micro-syringe, and was left to stand at room temperature (25° C.) a whole day. After left to stand a whole day, the gas was picked up in an amount of 5 mL out of the bottle by using a gas-tight syringe, and the amount of methyl mercaptan in the gas was measured by using the purge-and-trap gas chromatograph mass spectrometer (P&T-GCMS).

4. Calculating the Amount of Deodorizing the Methyl Mercaptan

By using the micro-syringe, 5 μL of the methyl mercaptane of a concentration of 650 ppm was injected as a bad-smelling substance into the 500-mL glass bottle purged with the nitrogen gas and of which the mouth was sealed with the rubber plug. Next, the gas was picked up in an amount of 5 mL out of the bottle by using the gas-tight syringe, and the amount of methyl mercaptane in the gas before being deodorized was measured by using the purge-and-trap gas chromatograph mass spectrometer (P&T-GCMS).

The amount of methyl mercaptan in the gas after left to stand a whole day was subtracted from the amount of methyl mercaptan in the gas before being deodorized to find the amount the methyl mercaptan that was deodorized.

5. Confirming the Infrared-Ray Absorption Peaks Near 1518 cm$^{-1}$

The films obtained in Examples 1 to 8, 10 to 15 and in Comparative Examples 1 to 12 and the primer coating of the primer-coated film obtained in Example 9 were measured to confirm their infrared-ray absorption peaks near 1518 cm$^{-1}$ derived from a bond between the organic acid component and the metal relying on a total reflection measuring method which is a customary method by using a Fourier transform infrared spectrophotometer (manufactured by Digilabo Japan Co.).

6. Functional Evaluation of Offensive Odor

After having measured the amount of methyl mercaptan in 3 above, the glass bottles sealed with rubber plugs were unsealed and were functionally evaluated for their offensive odor in the bottles by four panelists. The bottles without offensive odor from methyl mercaptan were evaluated to be ○ and the bottles smelling offensive were evaluated to be X.

7. Evaluating the Appearance

The films obtained in Examples 1 to 8, 10 to 15 and in Comparative Examples 1 to 12 and the primer-coated film obtained in Example 9 were confirmed by eyes for the presence of aggregation of particles. The films without aggregation and having excellent appearance were evaluated to be ○, and the films having aggregation and poor appearance were evaluated to be X.

8. Measuring the Residual Concentration of VOC Before the Adsorption

An aqueous solution containing 1.5% of a formaldehyde as a VOC was prepared. A 50-ML glass bottle purged with a nitrogen gas was sealed with a rubber plug. Thereafter, 5 μL of the aqueous solution containing 1.5% of the formaldehyde was injected into the bottle by using a micro-syringe and was left stand at room temperature (25° C.) for a whole day. After left to stand, a formaldehyde detector tube (manufactured by Gastec Co.) was inserted in the bottle to measure the concentration before the adsorption. The same measurement was also taken for an acetaldehyde.

9. Measuring the Residual Concentration of VOC after the Adsorption

The films obtained in Examples 1 to 8, 10 to 15 and in Comparative Examples 1 to 12 and the primer-coated film obtained in Example 9 were introduced into the 500-mL glass bottle purged with the nitrogen gas and were sealed. Thereafter, 5 μL of 1.5% formaldehyde was injected into the bottle by using the micro-syringe and was left stand at room temperature (25° C.) for a whole day. After left to stand, the formaldehyde detector tube (manufactured by Gastec Co.) was inserted in the bottle to measure the concentration after the adsorption. The same measurement was also taken for the acetaldehyde.

10. Calculating the Rate of Adsorbing the VOC

The residual concentration thereof after the adsorption was subtracted from the residual concentration of formaldehyde before the adsorption to find the amount of adsorption. The same calculation was also conducted for the acetaldehyde.

Example 1

5 Kilograms of a low-density polyethylene resin was blended with a silver myristate having an average particle diameter of 100 μm so that the content thereof was 0.1 wt %, and was extruded by using a biaxial extruder (manufactured by Toyo Seiki Seisakusho Co.) at an extrusion-forming temperature of 220° C. to prepare a film of a thickness of 50 μm in order to measure the amount of the methyl mercaptan, to calculate the amount the methyl mercaptan was deodorized and to confirm and evaluate the infrared-ray absorption peak near 1518 cm$^{-1}$. The results were as shown in Table 2.

Example 2

A film was prepared in the same manner as in Example 1 but blending the silver myristate in an amount of 0.5 wt %, and was measured, calculated, confirmed and evaluated. The results were as shown in Table 2.

Example 3

A film was prepared in the same manner as in Example 1 but blending the silver myristate in an amount of 1.0 wt %, and was measured, calculated, confirmed and evaluated. The results were as shown in Table 2.

Example 4

A film was prepared in the same manner as in Example 1 but blending the silver myristate in an amount of 1.5 wt %, and was measured, calculated, confirmed and evaluated. The results were as shown in Table 2.

Example 5

A film was prepared in the same manner as in Example 2 but at an extrusion-forming temperature of 190° C., and was measured, calculated, confirmed and evaluated. The results were as shown in Table 2.

Example 6

A film was prepared in the same manner as in Example 1 but blending a silver stearate having an average particle diameter of 100 μm in an amount of 0.5 wt %, and was measured, calculated, confirmed and evaluated. The results were as shown in Table 2.

Example 7

A film was prepared in the same manner as in Example 2 but at an extrusion-forming temperature of 250° C., and was measured, calculated, confirmed and evaluated. The results were as shown in Table 2.

Example 8

A film was prepared in the same manner as in Example 2 but at an extrusion-forming temperature of 270° C., and was measured, calculated, confirmed and evaluated. The results were as shown in Table 2.

Example 9

A high-molecular bisphenol type epoxy resin, a phenol formaldehyde resin (resol type) solution, a curing catalyst (phosphoric acid) and a silver myristate having an average particle diameter of 100 μm were mixed and stirred at a resin component ratio of 46:46:3:5. By using a mixed solvent (cyclohexanone:MIBK:MEK=1:1:1), a primer was so prepared that the concentration of the coating resin components was 20%. Onto a biaxially oriented PET/I (terephthalic acid/isophthalic acid=88/12) copolymer polyester film of a thickness of 50 μm, the primer was so applied that the dry weight thereof was 0.6 g/m² followed by drying at 180° C. to prepare a primer-coated film which was then measured, calculated, confirmed and evaluated. The results were as shown in Table 2.

Comparative Example 1

A film was prepared in the same manner as in Example 1 but blending a zeolite having an average particle diameter of 2 μm (manufactured by Mizusawa Kagaku Kogyo Co.) in an amount of 0.5 wt %, and was measured, calculated, confirmed and evaluated. The results were as shown in Table 2.

Comparative Example 2

A film was prepared in the same manner as in Example 1 but blending a commercially available inorganic deodorant having an average particle diameter of 1 μm (KESUMON, registered trade name, manufactured by Toa Gosei Co.) in an amount of 0.5 wt %, and was measured, calculated, confirmed and evaluated. The results were as shown in Table 2.

Comparative Example 3

A film was prepared in the same manner as in Comparative Example 2 but blending the inorganic deodorant in an amount of 2.0 wt %, and was measured, calculated, confirmed and evaluated. The results were as shown in Table 2.

Comparative Example 4

A film was prepared in the same manner as in Example 1 but blending silver having an average particle diameter of 100 nm in an amount of 0.5 wt %, and was measured, calculated, confirmed and evaluated. The results were as shown in Table 2.

Comparative Example 5

A film was prepared in the same manner as in Example 1 but blending silver having an average particle diameter of 4.5 μm in an amount of 0.5 wt %, and was measured, calculated, confirmed and evaluated. The results were as shown in Table 2.

Comparative Example 6

A film was prepared in the same manner as in Example 1 but blending silver oxide having an average particle diameter of 100 μm in an amount of 0.5 wt %, and was measured, calculated, confirmed and evaluated. The results were as shown in Table 2.

Comparative Example 7

A film was prepared in the same manner as in Example 1 but blending a silver stearate having a particle diameter of 1 to 100 nm obtained by heating, in an inert gas atmosphere at a temperature of 250° C., a silver stearate that was formed by a known method in an amount of 0.5 wt %, and was measured, calculated, confirmed and evaluated. The results were as shown in Table 2.

TABLE 2

| | Composition (starting material) | Content of ptcls. (wt %) | Extrusion-forming temp. (° C.) | Ave. ptcl. diameter after extrusion-forming (nm) | Amount of methyl mercaptan (ng) in 5 ml after left to stand a whole day | Deodorized amount (ng) |
|---|---|---|---|---|---|---|
| Ex. 1 | silver myristate | 0.1 | 220 | 10 | 1.566 | 656 |
| Ex. 2 | silver myristate | 0.5 | 220 | 12 | 1.35 | 677 |

TABLE 2-continued

| | Composition (starting material) | Content of ptcls. (wt %) | Extrusion-forming temp. (° C.) | Ave. ptcl. diameter after extrusion-forming (nm) | Amount of methyl mercaptan (ng) in 5 ml after left to stand a whole day | Deodorized amount (ng) |
|---|---|---|---|---|---|---|
| Ex. 3 | silver myristate | 1 | 220 | 10 | 1.22 | 690 |
| Ex. 4 | silver myristate | 1.5 | 220 | 9 | 1.657 | 646 |
| Ex. 5 | silver myristate | 0.5 | 190 | 50 | 2.063 | 606 |
| Ex. 6 | silver stearate | 0.5 | 220 | 11 | 1.835 | 629 |
| Ex. 7 | silver myristate | 0.5 | 250 | 20 | 2.122 | 600 |
| Ex. 8 | silver myristate | 0.5 | 270 | 30 | 1.987 | 613 |
| Ex. 9 | silver myristate | 1 | 180* | 100 | 2.2 | 592 |

| | Infrared absorption peak near $1518\ cm^{-1}$ | Functional evaluation | Evaluation of appearance |
|---|---|---|---|
| Ex. 1 | ○ | ○ | ○ |
| Ex. 2 | ○ | ○ | ○ |
| Ex. 3 | ○ | ○ | ○ |
| Ex. 4 | ○ | ○ | ○ |
| Ex. 5 | ○ | ○ | ○ |
| Ex. 6 | ○ | ○ | ○ |
| Ex. 7 | ○ | ○ | ○ |
| Ex. 8 | ○ | ○ | ○ |
| Ex. 9 | ○ | ○ | ○ |

| | Composition (starting material) | Content of ptcls. (wt %) | Extrusion-forming temp. (° C.) | Ave. ptcl. diameter after extrusion-forming (nm) | Amount of methyl mercaptan (ng) in 5 ml after left to stand a whole day | Deodorized amount (ng) |
|---|---|---|---|---|---|---|
| Comp. Ex. 1 | zeolite | 0.5 | 220 | 2000 | 3.5 | 462 |
| Comp. Ex. 2 | inorg. deodorant | 0.5 | 220 | 1200 | 5.407 | 271 |
| Comp. Ex. 3 | inorg. deodorant | 2 | 220 | 1200 | 6.92 | 120 |
| Comp. Ex. 4 | silver | 0.5 | 220 | 1000 | 6.442 | 168 |
| Comp. Ex. 5 | silver | 0.5 | 220 | 5000 | 7.785 | 34 |
| Comp. Ex. 6 | silver oxide | 0.5 | 220 | 500 | 7.478 | 64 |
| Comp. Ex. 7 | silver stearate | 0.5 | 220 | 150 | 3.12 | 500 |

| | Infrared absorption peak near $1518\ cm^{-1}$ | Functional evaluation | Evaluation of appearance |
|---|---|---|---|
| Comp. Ex. 1 | X | X | ○ |
| Comp. Ex. 2 | X | X | ○ |
| Comp. Ex. 3 | X | X | ○ |
| Comp. Ex. 4 | X | X | X |
| Comp. Ex. 5 | X | X | X |
| Comp. Ex. 6 | X | X | X |
| Comp. Ex. 7 | X | X | X |

*drying temperature

Example 10

5 Kilograms of a low-density polyethylene resin was blended with a silver stearate having an average particle diameter of 100 μm so that the content thereof was 0.5 wt %, and was extruded by using a biaxial extruder (manufactured by Toyo Seiki Seisakusho Co.) at an extrusion-forming temperature of 220° C. to prepare a film of a thickness of 50 μm in order to measure the amounts the VOCs, i.e., formaldehyde and acetaldehyde that were adsorbed, to measure the residual concentrations thereof after the adsorption, to calculate the amounts of adsorption, and to confirm and evaluate the infrared-ray absorption peak near $1518\ cm^{-1}$. The results were as shown in Table 3.

Example 11

A film was prepared in the same manner as in Example 10 but blending the silver stearate in an amount of 1.0 wt %, and was measured, calculated, confirmed and evaluated. The results were as shown in Table 3.

Example 12

A film was prepared in the same manner as in Example 10 but blending the silver stearate in an amount of 1.5 wt %, and was measured, calculated, confirmed and evaluated. The results were as shown in Table 3.

Example 13

A film was prepared in the same manner as in Example 10 but blending the silver myristate having an average particle diameter of 100 μm in an amount of 0.5 wt %, and was measured, calculated, confirmed and evaluated. The results were as shown in Table 3.

Example 14

A film was prepared in the same manner as in Example 10 but at an extrusion-forming temperature of 190° C., and was measured, calculated, confirmed and evaluated. The results were as shown in Table 3.

Example 15

A film was prepared in the same manner as in Example 10 but at an extrusion-forming temperature of 250° C., and was measured, calculated, confirmed and evaluated. The results were as shown in Table 3.

Example 16

A film was prepared in the same manner as in Example 10 but at an extrusion-forming temperature of 270° C., and was measured, calculated, confirmed and evaluated. The results were as shown in Table 3.

Comparative Example 8

A film was prepared in the same manner as in Example 10 but blending a zeolite having an average particle diameter of 2 μm (manufactured by Mizusawa Kagaku Kogyo Co.) in an amount of 0.5 wt %, and was measured, calculated, confirmed and evaluated. The results were as shown in Table 3.

Comparative Example 9

A film was prepared in the same manner as in Example 10 but blending a commercially available inorganic deodorant having an average particle diameter of 1 μm (KESUMON, registered trade name, manufactured by Toa Gosei Co.) in an amount of 0.5 wt %, and was measured, calculated, confirmed and evaluated. The results were as shown in Table 3.

Comparative Example 10

A film was prepared in the same manner as in Comparative Example 10 but blending silver having an average particle diameter of 100 nm in an amount of 0.5 wt %, and was measured, calculated, confirmed and evaluated. The results were as shown in Table 3.

Comparative Example 11

A film was prepared in the same manner as in Example 10 but blending silver having an average particle diameter of 4.5 μm in an amount of 0.5 wt %, and was measured, calculated, confirmed and evaluated. The results were as shown in Table 3.

Comparative Example 12

A film was prepared in the same manner as in Example 10 but blending a silver stearate having a particle diameter of 1 to 100 nm obtained in Comparative Example 7 in an amount of 0.5 wt %, and was measured, calculated, confirmed and evaluated. The results were as shown in Table 3.

TABLE 3

|  | Composition (starting material) | Content of ptcls. (wt %) | Extrusion-forming temp. (° C.) | Ave. ptcl. diameter after extrusion-forming (nm) |
|---|---|---|---|---|
| Ex. 10 | silver stearate | 0.5 | 220 | 11 |
| Ex. 11 | silver stearate | 1.0 | 220 | 15 |
| Ex. 12 | silver stearate | 1.5 | 220 | 8 |
| Ex. 13 | silver myristate | 0.5 | 220 | 12 |
| Ex. 14 | silver stearate | 0.5 | 190 | 50 |
| Ex. 15 | silver myristate | 0.5 | 250 | 12 |
| Comp. Ex. 8 | zeolite | 0.5 | 220 | 2000 |
| Comp. Ex. 9 | inorg. deodorant | 0.5 | 220 | 1200 |
| Comp. Ex. 10 | silver | 2.0 | 220 | 1000 |
| Comp. Ex. 11 | silver | 0.5 | 220 | 5000 |
| Comp. Ex. 12 | silver stearate | 0.5 | 220 | 150 |

|  | Formaldehyde | | | Acetaldehyde | | |
|---|---|---|---|---|---|---|
|  | Concentration before adsorption (ppm) | Concentration after adsorption (ppm) | Amount of adsorption (ppm) | Concentration before adsorption (ppm) | Concentration after adsorption (ppm) | Amount of adsorption (ppm) |
| Ex. 10 | 31.0 | 17.0 | 14.0 | 17.0 | 9.0 | 8.0 |
| Ex. 11 | 31.0 | 13.0 | 18.0 | 17.0 | 8.5 | 8.5 |
| Ex. 12 | 31.0 | 16.0 | 15.0 | 17.0 | 8.0 | 9.0 |

TABLE 3-continued

| | | | | | | |
|---|---|---|---|---|---|---|
| Ex. 13 | 31.0 | 16.0 | 15.0 | 17.0 | 9.5 | 7.5 |
| Ex. 14 | 31.0 | 18.0 | 13.0 | 17.0 | 9.5 | 7.5 |
| Ex. 15 | 31.0 | 18.0 | 13.0 | 17.0 | 9.5 | 7.5 |
| Comp. Ex. 8 | 31.0 | 26.0 | 5.0 | 17.0 | 12.5 | 4.5 |
| Comp. Ex. 9 | 31.0 | 21.0 | 10.0 | 17.0 | 14.0 | 3.0 |
| Comp. Ex. 10 | 31.0 | 26.0 | 5.0 | 17.0 | 13.0 | 4.0 |
| Comp. Ex. 11 | 31.0 | 28.0 | 3.0 | 17.0 | 15.0 | 2.0 |
| Comp. Ex. 12 | 31.0 | 22.5 | 8.5 | 17.0 | 11.0 | 6.0 |

| | Infrared absorption peak near 1518 cm$^{-1}$ | Evaluation of appearance |
|---|---|---|
| Ex. 10 | ○ | ○ |
| Ex. 11 | ○ | ○ |
| Ex. 12 | ○ | ○ |
| Ex. 13 | ○ | ○ |
| Ex. 14 | ○ | ○ |
| Ex. 15 | ○ | ○ |
| Comp. Ex. 8 | X | ○ |
| Comp. Ex. 9 | X | ○ |
| Comp. Ex. 10 | X | X |
| Comp. Ex. 11 | X | X |
| Comp. Ex. 12 | X | X |

The invention claimed is:

1. A coating composition containing adsorptive ultra-fine metal particles having a bond between an organic acid component and a metal, and exhibiting an infrared absorption peak derived from the bond between the organic acid component and the metal at 1518 cm$^{-1}$, said organic acid being at least one fatty acid selected from myristic acid, stearic acid, oleic acid, palmitic acid, n-decanoic acid, para-toluic acid, succinic acid, malonic acid, tartaric acid, malic acid, glutalic acid, adipic acid and acetic acid, and said ultra-fine metal particles being formed by heating said coating composition, having an average particle diameter of 1 to 100 nm being and having said fatty acid present on the surfaces thereof, said coating composition further containing a coating component selected from the group consisting of an acrylic coating material, an epoxy coating material, a phenol coating material, a urethane coating material, and an alkyd resin coating material.

2. The resin composition according to claim 1, wherein said metal is at least any one of gold, silver or copper.

3. The resin composition according to claim 1, wherein said resin composition has a coefficient of oxygen permeation of not smaller than $1.0 \times 10^{-4}$ cc·m/m$^2$·day·atm.

* * * * *